United States Patent [19]

Van Aspert

[11] Patent Number: 4,688,278
[45] Date of Patent: Aug. 25, 1987

[54] APPARATUS SUITABLE FOR USE IN METHODS OF EXAMINATION, INTENDED IN PARTICULAR FOR PERSONS

[75] Inventor: Joan J. A. M. Van Aspert, ZG Heeswijk, Netherlands

[73] Assignee: Askové Kunststof Industrie B.V., Heeswijk, Netherlands

[21] Appl. No.: 786,794

[22] Filed: Oct. 11, 1985

[30] Foreign Application Priority Data

Oct. 15, 1984 [NL] Netherlands ............ 8403133

[51] Int. Cl.⁴ .................................... A61G 7/08
[52] U.S. Cl. ...................... 5/81 B; 378/209; 250/453.1
[58] Field of Search ........... 5/81 R, 81 B, 86, 82 R; 312/335, 341, 345; 250/453.1, 454.1, 455.1; 340/551, 562, 573; 324/260; 378/209; 52/36, 309.1

[56] References Cited

U.S. PATENT DOCUMENTS 3,840,221 10/1974 Hogan ............................. 5/82 X
4,105,923 8/1978 Hynes, Jr. ..................... 250/456
4,259,756 4/1981 Pace ................................. 5/81 B
4,365,344 12/1982 Dornheim ................. 378/209 X

FOREIGN PATENT DOCUMENTS 0077447 4/1983 European Pat. Off. ......... 250/453.1
1949904 10/1969 Fed. Rep. of Germany ...... 378/209
2012157 10/1971 Fed. Rep. of Germany ... 250/453.1
1566126 9/1976 Fed. Rep. of Germany ... 250/453.1
2613863 10/1977 Fed. Rep. of Germany ...... 378/209
2759079 7/1979 Fed. Rep. of Germany ...... 378/209
2528692 12/1983 France ............................. 250/453.1
1435223 5/1976 United Kingdom ............... 378/209

Primary Examiner—Carl D. Friedman
Assistant Examiner—Naoko N. Slack
Attorney, Agent, or Firm—Majestic, Gallagher, Parsons & Siebert

[57] ABSTRACT

An apparatus suitable for environments where the presence of metals or traces of metals is inadmissible, consisting of a combination of a stretcher with a movable undercarriage, whereby both stretcher and undercarriage have been made virtually entirely in plastic, consisting of a thermoplastic material, the apparatus being absolutely free of metals.

9 Claims, 5 Drawing Figures

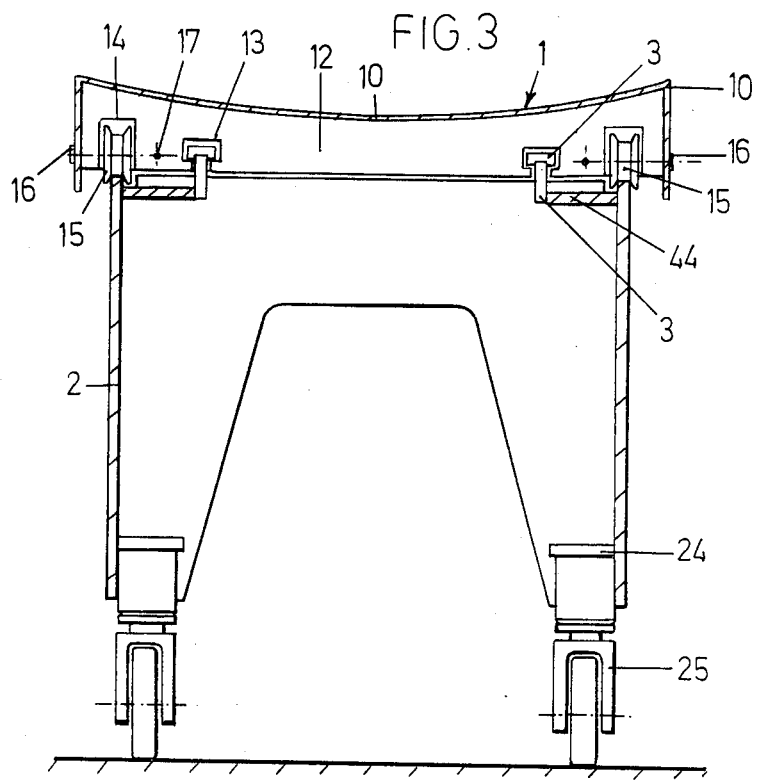
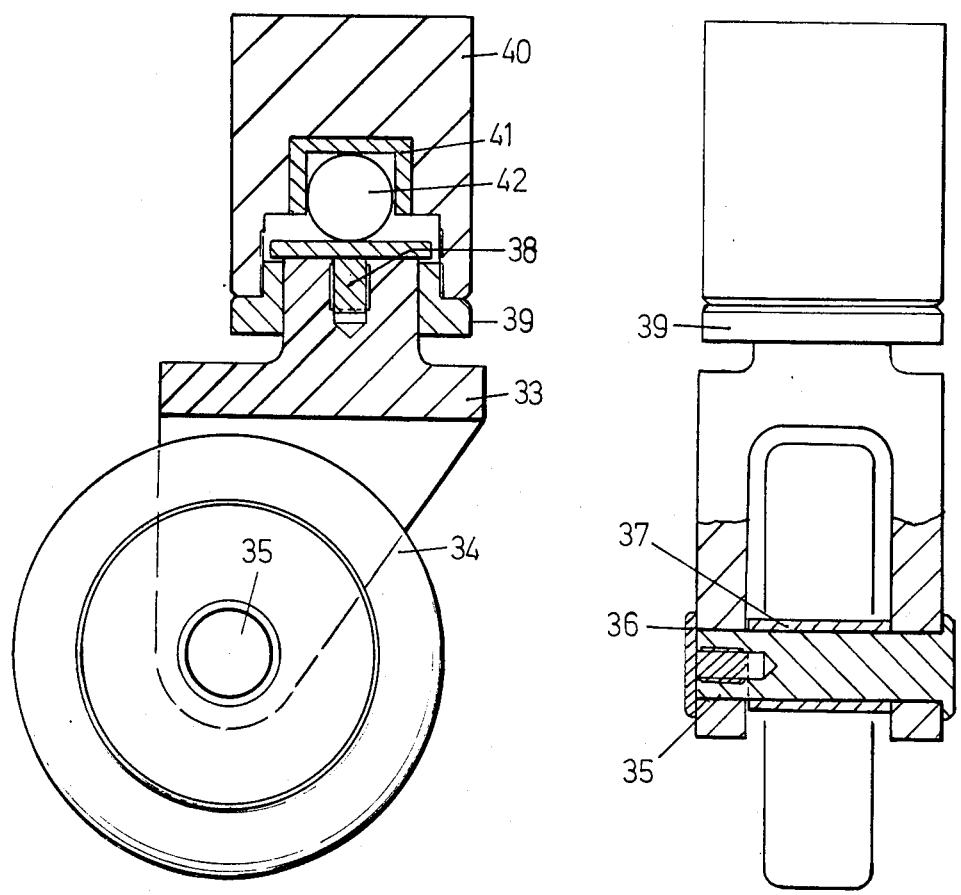

APPARATUS SUITABLE FOR USE IN METHODS OF EXAMINATION, INTENDED IN PARTICULAR FOR PERSONS

The invention relates to apparatus suitable for use in methods of examination, intended in particular for persons, where the presence of metals or traces of metals is inadmissible.

There is a need of such an apparatus for passing persons or objects by non-metallic means through a metal detector in general and for moving persons or objects in environments where metallic means of transportation must not be used in view of the presence of strong magnetic fields, such as those employed in modern methods of examination. In addition, the apparatus or parts thereof may be applied in spaces where metallic means of transportation are inadmissible on account of chemical action. As such examinations often serve medical purposes and therefore involve patients as a rule, the invention consequently relates to an apparatus consisting of a combination of a stretcher with a movable undercarriage.

The above-mentioned requirements are satisfied by an apparatus of the said type, characterized in that both stretcher and undercarriage have been made virtually entirely in plastic, consisting of a thermoplastic material, the apparatus being absolutely free of metals. The invention finds application in particular with new methods for internal examination of patients, which in many cases replace the well-known X-ray examination.

In spaces where the examination is conducted according to novel methods of analysis, no steel must be present. Steel has a fatal influence on the strong magnets and the fluid employed in these modern systems; hence the requirement of an absolutely non-metallic construction which is, in addition, to be sufficiently strong, movable and disinfectable.

Accordingly, the apparatus according to the invention is also characterized in that the stretcher is connected to the undercarriage by means of a T-shaped guide rail and locking device, from which it can be disengaged by a relative displacement in the long direction relative to the undercarriage along the guide rail after releasing of the locking device.

The T-shaped guide ensures that the stretcher remains firmly attached to the undercarriage also when in a tilted or an oblique position, whilst the locking device obviously prevents displacement of the stretcher relative to the undercarriage during transport.

According to the invention, a metal detector may be present for a person to be checked for the presence of metal parts, whilst a combination of stretcher and undercarriage may be moved right alongside the detector, which is provided with a bridge mounted on bridge supports and with a bridge guide member in such a fashion that the stretcher can be transferred from one undercarriage to another undercarriage via the guide member of the detector bridge.

The stretcher preferably comprises a top surface provided at both ends with a handle and on its underside with a number of transversely mounted strengthening ribs having T-shaped recesses for passing the guide rail through as well as recesses which accommodate doubleflanged running wheels resting on the top edges of the undercarriage which edges are so designed as to serve as flat rails supporting the running wheels when the stretcher is in position on the undercarriage, whilst the stretcher is provided at one end with a bumper which acts in concert with an arresting pin of a locking device mounted in the undercarriage.

According to the invention, the undercarriage comprises a rectangular frame designed in the shape of a table with strengthening ribs mounted transversely at the top such that the flat top edge of the frame is kept free for the runing wheels of the stretcher on both sides in the long direction, whilst the said frame is furthermore provided in the long direction with two parallel guide strips disposed above the strengthening ribs, and a locking device for the stretcher is mounted on the frame at one end, while at each of the bottom corners of the frame a wheel cap is attached to which a swivel castor system is fitted.

In a preferred embodiment of the invention, the locking device comprises a leaf spring which tapers in the long direction towards the end of the undercarriage and whose broad end has been fixed under a slight angle from the horizontal plane in a clamping holder attached to a strengthening rib in such a fashion that the leaf spring tends to bounce up from this horizontal plane, whilst the narrow end carries a handle which passes through a slit in the frame so as to end outside the frame, and on top of the narrow end an arresting pin is present which interacts with a bumper forming part of the stretcher.

The swivel castors may consist of disc-type wheels enclosed in a yoke which is rotatably encased in a bearing housing by means of a pressure bolt with a collar flange, whilst the said bearing housing also accommodates a ball encased in a holder, in such a fashion that the combination of wheel yoke and collar flange rests against the ball.

Obviously, it is very important that the full weight of the person or patient to be examined can safely be applied to two wheels, and perhaps even to one. Hence, sufficient strength and stiffness of the assembly are prerequisites. A further important requirement is resistance to a rise in temperature, having regard to both cleaning and disinfection of the assembly in view of its potential use in hospitals. By the employment of different types of plastics and special methods of fabrication, such as hot-gas welding and mechanical joints, an apparatus usable for the situation defined has been developed.

Thus, the top of the stretcher and the strengthening ribs have been made of high-molecular-weight polyethylene, and the running wheels of hard polyurethane with a polyacetate spindle. The frame of the undercarriage, including the wheel cap, guide strips and strengthening ribs, wholly consists of high-molecular-weight polyethylene, and the various parts are interconnected by means of screws and bolts made in polyamide. The leaf spring consists of a fabric of bisphenol with textile and other parts of the locking device of high-molecular-weight polyethylene, whilst again screws or bolts in polyamide have been applied for connecting the component parts together. The yoke is made of polyacetate, and the bearing housing of high-molecular-weight polyethylene, whilst the bearing bushing, holder and pressure bolt are made of polyethylene terephthalate and the ball is of hardened glass.

The invention will now be elucidated with reference to the drawings in which an embodiment of the apparatus according to the invention is represented by way of example. In the drawings:

FIG. 1 presents a top view of an assembly comprising a combination of a stretcher and an undercarriage alongside a metal detector, whilst on the other side of this detector an undercarriage is placed in position for receiving the stretcher when the latter has moved past the detection device;

FIG. 3 represents a cross-section taken along the line III—III of FIG. 2; and

FIGS. 4 and 5 represent a cross-section and a partially cross-sectional front elevation perpendicular thereto, respectively, of a swivel castor design according to the invention on a somewhat enlarged scale.

Figure 1:
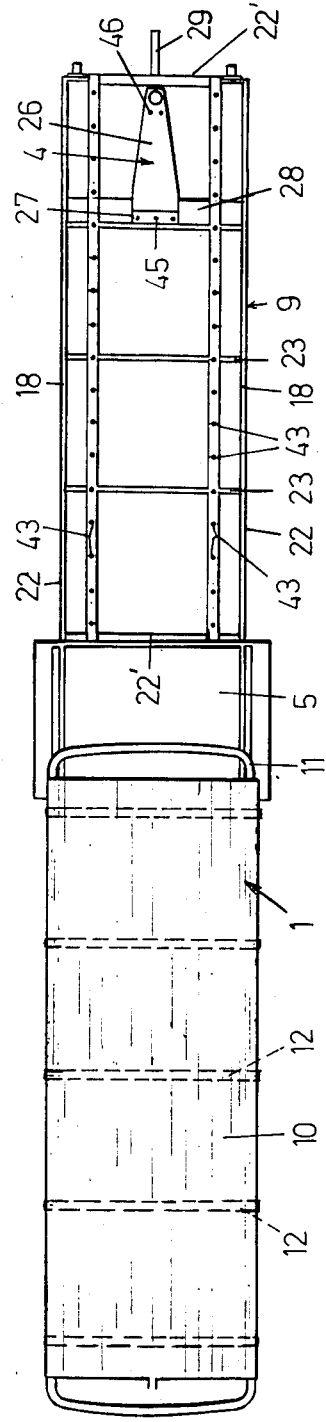
Figure 2:
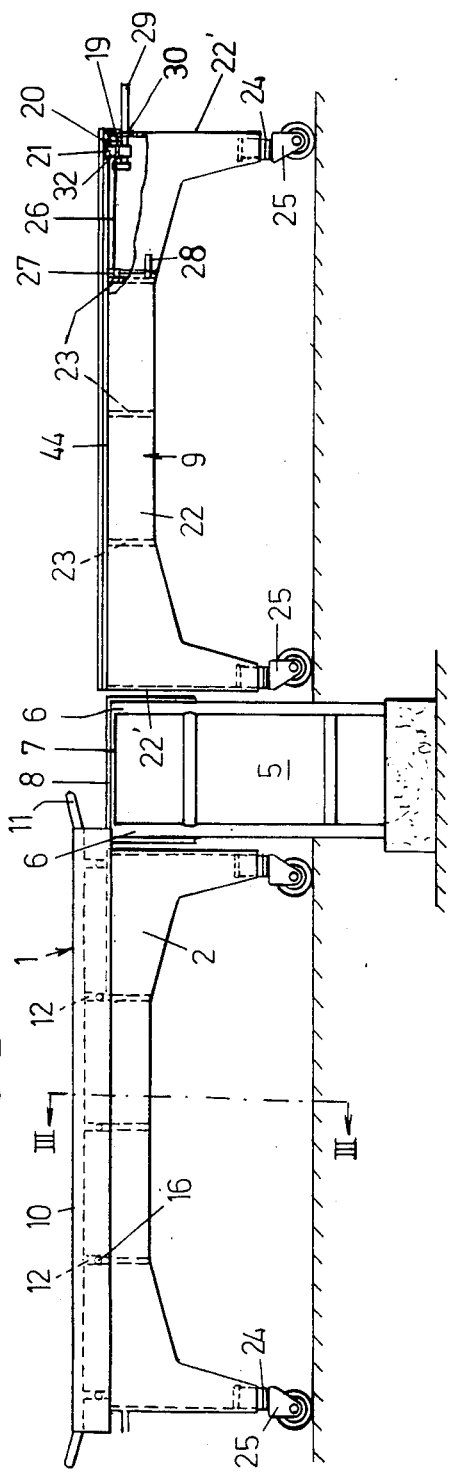
FIG. 2 represents a lateral view of the assembly according to FIG. 1.

In the figures a stretcher 1 is connected to a movable undercarriage 2, and these are interconnected by means of a T-shaped guide rail 3 with a locking device 4.

Alongside this assembly there is a metal detector 5 which is provided with bridge supports 6, on which is mounted a bridge 7 carrying a bridge guide member 8. On the other side of the metal detector 5 a movable undercarriage 9 is disposed for the reception of the stretcher after its passage along the metal detector 5.

The stretcher comprises a top 10 provided with a handle 11 as well as with transverse strengthening ribs 12. These ribs 12 have T-shaped recesses 13 through which the T-shaped guide rail 3 is passed with some play in order to permit displacement in the long direction. Also, a recess 14 is present for accommodating the running wheels 15, which are connected to the stretcher by means of a wheel axle 16 with lock pin 17.

The top edges 18 of the undercarriage have the form of a flat rail on which the double-flanged running wheels 15 of the stretcher can move in the longitudinal direction.

At the end of the undercarriage, a bumper 19 is provided, having a bumper edge 20 which in combination with an arresting pin 21 can lock the stretcher in position on the undercarriage. The undercarriage moreover comprises a frame, consisting of two longitudinal panels 22 as indicated in the figure as well as two transverse panels 22' serving as end faces with a number of strengthening ribs 23 mounted in between. Furthermore, a wheel cap 24 has been fitted to each foot to permit a swivel castor system 25 to be attached thereto.

The locking device consists of a leaf spring 26, fastened in a clamping holder 27 under a slight angle of approximately 10° from the horizontal plane. Underneath the leaf spring 26 with clamping holder 27 a spring-support panel 28 has been mounted. Leaf spring 26 tapers towards the end of the undercarriage, at which point an arresting pin 21 is also attached to the leaf spring with the aid of a securing ring 32. Furthermore, a handle 29 has been fitted at the very same location by means of an axle bearing passed through the base of the arresting pin 21, which handle is caused to protrude outside through a slit 30 and with which the leaf spring can be moved up and down by means of the handle being attached to leaf spring 26 by mounting member 31 in order to release the stretcher.

The FIGS. 4 and 5 represent the swivel castor design 25 on an enlarged scale, partly in cross-section, partly in front view. The design features a yoke 33 in which a disc-type wheel 34 is fitted with the aid of a wheel axle 35 with pressure bolt 36, on which axle a bearing bushing 37 is mounted as well. The yoke itself is encased by means of a pressure bolt with collar flange 38 and a ring bearing 39 in the bearing housing 40. Within this bearing housing a space is provided which accommodates a hardened-glass ball 42 confined in a holder 41, which ball rests against the collar flange of the pressure bolt 38.

In the embodiment specified, the T-shaped guide member is provided with mounting ribs 44, whilst the guide itself is composed of two parts, of which the upper plane one is attached to the lower one by means of tap bolts 43.

This arrangement has the advantage that in case of wear only the upper part of the guide member need be replaced. For the same reason the leaf spring 26 is attached to the associated parts by means of tap bolts 45 and 46, respectively.

The concept underlying the set-up described in this example is that the undercarriage is first, with the stretcher, moved to a detection device, whereupon the stretcher is rolled to the other side of the centrally positied detector onto a second undercarriage. This transfer is necessary for establishing whether the patient carries metal parts in any form whatsoever inside his or her body, such as, for instance, a pace-maker, steel pins and probably also dental prostheses. Subsequenly the patient, if proved completely free of metals, can be admitted with the undercarriage and the stretcher to the diagnostic unit.

It will be clear that the combination of stretcher or bed with the undercarriage can be provided on one side only with a locking device as described, that is to say, in the set-up described hereinbefore on that side which is farther removed from the detection device. Otherwise, it would obviously be impossible to slide the stretcher or the bed from the undercarriage and transfer it via the detection device to the other undercarriage.

In point of fact, the invention is not restricted either to the embodiment described or to the application specified. Thus, it is also possible, for example, that the combination of the stretcher or the bed with the undercarriage is employed in a suitably adapted version for other types of metal detection, for instance, in the food or pharmaceutical industry, or more generally in the chemical industry.

I claim:

1. Apparatus suitable for use in methods of examination, intended in particular for persons, where the presence of metals or traces of metals is inadmissible, consisting of a combination of a stretcher with a movable undercarriage, characterized in that both stretcher and undercarriage have been made virtually entirely of plastic, consisting of a thermoplastic material, the apparatus being absolutely free of metals, the stretcher being operatively connected to said undercarriage by means of a T-shaped guide rail and a locking device, from which it can be disengaged by a relative displacement in the longitudinal direction in relation to the undercarriage along the guide rail after releasing of the locking device, and wherein the stretcher comprises a top surface provided at both ends with a handle and on its underside with a number of transversely mounted strengthening ribs having recesses for passing the guide rail through as well as recesses which accommodate double-flanged running wheels resting on the topmost edges of the undercarriage which are so designed as to serve as flat rails for the said wheels when the stretcher is positioned on the undercarriage, while the stretcher is provided at one end with a bumper which acts in concert with an arresting pin of a locking device mounted in the undercarriage.

2. Apparatus according to claim 1 characterized in that the undercarriage comprises a rectangular frame designed in the shape of a table with strengthening ribs mounted transversely at the top such that on both sides in the long direction the flat top edge of the frame is kept free for the running wheels of the stretcher, while the said frame is furthermore provided in the long direction with two parallel guide strips disposed above the strengthening ribs, and a locking device for the stretcher is mounted on the frame at one end, while at each of the bottom corners of the frame a wheel cap is attached to which a swivel castor system is fitted.

3. Apparatus according to claim 2 characterized in that the swivel castors are disc-type wheels enclosed in a yoke which is rotatably encased in a bearing housing by means of a pressure bolt with a collar flange, while the said bearing housing also accommodates a ball confined within a holder, in such a fashion that the combination of wheel yoke and collar flange rests against the ball.

4. Apparatus according to claim 1 characterized in that the top surface of the stretcher and the strengthening ribs consist of high-molecular-weight polyethylene, while the running wheels are made of hard polyurethane with a polyacetate spindle.

5. Apparatus suitable for use in methods of examination intended in particular for persons, where the presence of metals or traces of metals is inadmissible, consisting of a combination of a stretcher with a movable undercarriage, characterized in that both stretcher and undercarriage have been made virtually entirely of plastic, consisting of a thermoplastic material, the apparatus being absolutely free of metals, the stretcher being operatively connected to said undercarriage by means of a guide rail and a locking device, from which it can be disengaged by a relative displacement in the longitudinal direction in relation to the undercarriage along the guide rail after releasing of the locking device, characterized in that the apparatus further includes a metal detector for allowing a person to be checked for the presence of metal parts, while said combination of stretcher and undercarriage may be moved up to a position alongside the detector, and further including a bridge mounted on bridge supports and a bridge guide member in such a fashion that the stretcher can be transferred from one undercarriage to another undercarriage via the guide member of the bridge.

6. Apparatus suitable for use in methods of examination intended in particular for persons, where the presence of metals or traces of metals is inadmissible, consisting of a combination of a stretcher with a movable undercarriage, characterized in that both stretcher and undercarriage have been made virtually entirely of plastic, consisting of a thermoplastic material, the apparatus being absolutely free of metals, the stretcher being operatively connected to said undercarriage by means of a guide rail and a locking device, from which it can be disengaged by a relative displacement in the longitudinal direction in relation to the undercarriage along the guide rail after releasing of the locking device, characterized in that the stretcher comprises a top surface provided at both ends with a handle and on its underside with a number of transversely mounted strengthening ribs having recesses for passing the guide rail through as well as recesses which accommodate double-flanged running wheels resting on the topmost edges of the undercarriage which are so designed as to serve as flat rails for the said wheels when the stretcher is positioned on the undercarriage, while the stretcher is provided at one end with a bumper which acts in concert with an arresting pin of a locking device mounted in the undercarriage, and wherein said locking device comprises an elongated leaf spring defining a long direction which tapers in the long direction towards the end of the undercarriage and whose broad end has been fixed under a slight angle from the horizontal plane in a clamping holder attached to a strengthening rib in such a fashion that the leaf spring tends to bounce up from this horizontal plane, while the narrow end carries a handle which passes through a slit in the frame so as to protrude from the frame, and on top of the narrow end an arresting pin is present which interacts with a bumper forming part of the stretcher.

7. Apparatus according to claim 6, characterized in that the leaf spring consists of a fabric of bisphenol with textile and the other parts of the locking device being made of high-molecular-weight polyethylene, while the various parts are again interconnected by means of polyamide screws or bolts.

8. Apparatus suitable for use in methods of examination intended in particular for persons, where the presence of metals or traces of metals is inadmissible, consisting of a combination of a stretcher with a movable undercarriage, characterized in that both stretcher and undercarriage have been made virtually entirely of plastic, consisting of a thermoplastic material, the apparatus being absolutely free of metals, the stretcher being operatively connected to said undercarriage by means of a guide rail and a locking device, from which it can be disengaged by a relative displacement in the longitudinal direction in relation to the undercarriage along the guide rail after releasing of the locking device, characterized in that the undercarriage comprises a rectangular frame designed in the shape of a table with strengthening ribs mounted transversely at the top such that on both sides in the long direction the flat top edge of the frame is kept free for the running wheels of the stretcher, while the said frame is furthermore provided in the long direction with two parallel guide strips disposed above the strengthening ribs, and a locking device for the stretcher is mounted on the frame at one end, while at each of the bottom corners of the frame a wheel cap is attached to which a swivel castor system is fitted, and wherein the frame of the undercarriage, including the wheel cap, guide strips and strengthening ribs are wholly made in high-molecular-weight polyethylene, while the various parts are interconnected by means of poyamide screws or bolts.

9. Apparatus suitable for use in methods of examination intended in particular for persons, where the presence of metals or traces of metals is inadmissible, consisting of a combination of a stretcher with a movable undercarriage, characterized in that both stretcher and undercarriage have been made virtually entirely of plastic, consisting of a thermoplastic material, the apparatus being absolutely free of metals, the stretcher being operatively connected to said undercarriage by means of a guide rail and a locking device, from which it can be disengaged by a relative displacement in the longitudinal direction in relation to the undercarriage along the guide rail after releasing of hte locking device, characterized in that the undercarriage comprises a rectangular frame designed in the shape of a table with strengthening ribs mounted transversely at the top such that on both sides in the long direction the flat top edge of the frame is kept free for the running wheels of the stretcher, while the said frame is furthermore provided in the long direction with two parallel guide strips disposed above the strengthening ribs, and a locking device for the stretcher is mounted on the frame at one end, while at each of the bottom corners of the frame a wheel cap is attached to which a swivel castor system is fitted, and wherein the swivel castors are disc-type wheels enclosed in a yoke which is rotatably encased in a bearing housing by means of a pressure bolt with a collar flange, while the said bearing housing also accommodates a ball confined within a holder, in such a fashion that the combination of wheel yoke and collar flange rests against the ball, and wherein the wheel yoke consists of polyacetate and the bearing housing is made in high-molecular-weight polyethylene, while the bearing bushing, holder and pressure bolt are constructed in polyethylene terephthalate and the ball consists of hardened glass.

* * * * *